United States Patent
Choi et al.

(10) Patent No.: US 11,426,421 B2
(45) Date of Patent: *Aug. 30, 2022

(54) COMPOSITION FOR PREVENTING OR IMPROVING INFLAMMATION INCLUDING EXTRACT OF SEED OF NEW SOYBEAN CULTIVAR SCEL-1

(71) Applicants: KOREA INSTITUTE OF SCIENCE AND TECHNOLOGY, Seoul (KR); REPUBLIC OF KOREA(MANAGEMENT : RURAL DEVELOPMENT ADMINISTRATION), Jeonju-si (KR)

(72) Inventors: Yongsoo Choi, Gangneung-si (KR); Jin-Chul Kim, Gangneung-si (KR); Su-Nam Kim, Gangneung-si (KR); Kyungsu Kang, Gangneung-si (KR); Seung-Hoon Yang, Gangneung-si (KR); Keunwan Park, Gangneung-si (KR); Hee Ju Lee, Gangneung-si (KR); Dae-geun Song, Gangneung-si (KR); Kwang-Hyun Cha, Gangneung-si (KR); Joo Yeong Jeon, Gangneung-si (KR); Chang Geon Kim, Gangneung-si (KR); Jung Kyung Moon, Wanju-gun (KR); Man Soo Choi, Changwon-si (KR); Soo Kwon Park, Wanju-gun (KR); Nam Hee Jeong, Jeonju-si (KR)

(73) Assignees: KOREA INSTITUTE OF SCIENCE AND TECHNOLOGY, Seoul (KR); REPUBLIC OF KOREA(MANAGEMENT : RURAL DEVELOPMENT ADMINISTRATION), Jeongju-si (KR)

( * ) Notice: Subject to any disclaimer, the term of this patent is extended or adjusted under 35 U.S.C. 154(b) by 481 days.

This patent is subject to a terminal disclaimer.

(21) Appl. No.: 16/212,116

(22) Filed: Dec. 6, 2018

(65) Prior Publication Data
US 2020/0009172 A1    Jan. 9, 2020

(30) Foreign Application Priority Data
Jul. 5, 2018   (KR) ................. 10-2018-0078247

(51) Int. Cl.
| | | |
|---|---|---|
| A61K 36/00 | (2006.01) | |
| A61K 31/7048 | (2006.01) | |
| A23L 33/105 | (2016.01) | |
| A61P 17/00 | (2006.01) | |
| A61P 29/00 | (2006.01) | |
| A61K 9/00 | (2006.01) | |
| A61K 31/352 | (2006.01) | |
| A61K 36/48 | (2006.01) | |

(52) U.S. Cl.
CPC ........ *A61K 31/7048* (2013.01); *A23L 33/105* (2016.08); *A61K 9/0014* (2013.01); *A61K 31/352* (2013.01); *A61K 36/48* (2013.01); *A61P 17/00* (2018.01); *A61P 29/00* (2018.01); *A23V 2002/00* (2013.01)

(58) Field of Classification Search
CPC ........................................ A61K 36/00
USPC ........................................ 424/725
See application file for complete search history.

(56) References Cited

U.S. PATENT DOCUMENTS

| | | | |
|---|---|---|---|
| 8,377,424 B2 | 2/2013 | Romanczyk, Jr. et al. | |
| 8,846,757 B2 | 9/2014 | D'Armiento et al. | |
| 2002/0054924 A1 | 5/2002 | Leahy et al. | |

FOREIGN PATENT DOCUMENTS

KR    10-1862265 B1    7/2017

OTHER PUBLICATIONS

Zhuang et al., Inflammation & Allergy—Drug Targets, 2014, 13, 153-161.*
International Search Report dated Apr. 2, 2019, in PCT/KR2018/015454.
Ito et al., "Characterisation of proanthocyanidins from black soybeans: Isolation and characterisation of proanthocyanidin oligomers from black soybean seed coats," Food Chemistry (2013), vol. 141, pp. 2507-2512.
Kanamoto et al., "A Black Soybean Seed Coat Extract Prevents Obesity and Glucose Intolerance by Up-regulating Uncoupling Proteins and Down-Regulating Inflammatory Cytokines in High-Fat Diet-Fed Mice," J. Agric. Food Chem. (2011), vol. 59, pp. 8985-8993.
Lee et al., "Comprehensive phenolic composition analysis and evaluation of Yak-Kong soybean (*Glycine max*) for the prevention of atherosclerosis," Food Chemistry (2017), vol. 234, pp. 486-493.
Written Opinion of the International Searching Authority dated Apr. 2, 2019, in PCT/KR2018/015454.
Fukami et al., "Isolation of a Reduced Form of Cyanidin 3-O-β-D-Glucoside from Immature Black Soybean (*Giycinemax* (L) Merr.) and its Reducing Properties", J. Oleo Sci., vol. 62, No. 8, 2013, pp. 623-629 (7 pages).

(Continued)

*Primary Examiner* — Michael V Meller
(74) *Attorney, Agent, or Firm* — Birch, Stewart, Kolasch & Birch, LLP

(57) ABSTRACT

Provided are a composition for preventing or improving inflammation, the composition including an extract of a seed of soybean *Glycine max* (L.) Merrill cultivar SCEL-1, and a method of preventing occurrence of inflammation in a subject or improving inflammation in a subject, the method including injecting the composition to a subject.

6 Claims, 2 Drawing Sheets

(56) References Cited

OTHER PUBLICATIONS

Cha et al., "Comparison of Antioxidant Activity and Composition in Glycine max Merr. and Glycine soja Siebold et Zucc.," Kor. J. Pharmacogn. 27(3), 1996, pp. 190-195.
Chengja3, Cultivar Application Publication No. 2005-176, 2005, 1 page.
Guideline, Soybean *Glycine max* (L.) Merrill, 2014, 21 pages.
Wonheug, Cultivar Application Publication No. 2010-341, 2010, 1 page.
Database WPI, Week 200960, Thomson Scientific, London, GB; AN 2009-F82163, XP 002790886 & KR 2009-0019396 A (Feb. 25, 2009).
Database WPI, Week 201774, Thomson Scientific, London, GB; AN 2017-714273, XP 002790887 & JP 2017-190355 A (Oct. 19, 2017).
Database WPI, Week 201806, Thomson Scientific, London, GB; AN 2018-00121T, XP 002790890 & KR 2017-0138351 A (Dec. 15, 2017).
Extended European Search Report dated May 10, 2019, in European Patent Application No. 18210806.8.
Imm, J.-Y. and S.-J. Kim, "Anti-cancer and Anti-inflammatory Effects of Mung Bean and Soybean Extracts," Korean Journal of Food Science and Technology (Dec. 31, 2010), vol. 42, No. 6, pp. 755-761, with English abstract.

\* cited by examiner

COMPOSITION FOR PREVENTING OR IMPROVING INFLAMMATION INCLUDING EXTRACT OF SEED OF NEW SOYBEAN CULTIVAR SCEL-1

CROSS-REFERENCE TO RELATED APPLICATION

This application claims the benefit of Korean Patent Application No. 10-2018-0078247, filed on Jul. 5, 2018, in the Korean Intellectual Property Office, the disclosure of which is incorporated herein in its entirety by reference.

BACKGROUND

1. Field

One or more embodiments relate to a composition for preventing or improving inflammation, the composition including an extract of a seed of soybean Glycine max (L.) Merrill cultivar SCEL-1, and a method of preventing occurrence of inflammation in a subject or improving inflammation in a subject, the method including injecting the composition to a subject.

2. Description of the Related Art

Soybeans are an abundant crop source of vegetable proteins, and contain not only proteins, but also a variety of excellent functional materials including unsaturated fatty acids, amino acids, isoflavones, and phenolic acids. In this regard, soybeans are being used as a protein source to replace animal proteins.

Researchers, CHA, Baecheon et al. (The Korean Society of Pharmacognosy, Vol. 27(3): pages 190-195 (published in 1996)), discovered that an extract obtained by performing an extraction process (hereinafter referred to as an ethanol extract) on a wild-type soybean Glycine soja Siebold et Zucc. by using ethanol contains (−)-epicatechin, unlike an ethanol extract of another soybean Glycine max (L.) Merrill. In addition, the researchers also discovered that the ethanol extract of the wild-type soybean has antioxidative activity, but did not disclose that the soybean contains (−)-epicatechin.

Therefore, there is a demand for a new soybean cultivar having excellent prevention or improvement function of inflammation, compared to the known soybeans, or for a composition including an extract obtained from the new soybean cultivar.

SUMMARY

One or more embodiments include a composition for preventing or improving inflammation, the composition including, as an active ingredient, an extract obtained by performing an extraction process on a seed of soybean Glycine max (L.) Merrill cultivar SCEL-1 by using water, $C_1$-$C_6$ alcohol, or a mixture thereof, wherein the seed contains cyanidin-3-O-glucoside, procyanidin B2, and epicatechin, wherein an amount of the procyanidin B2 is greater than that of the cyanidin-3-O-glucoside, and a representative sample of the seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

One or more embodiments include a composition for preventing or improving inflammation, the composition including, as active ingredients, cyanidin-3-O-glucoside or a physiologically acceptable salt thereof, procyanidin B2 or a physiologically acceptable salt thereof, and epicatechin or a physiologically acceptable salt thereof, at a weight ratio of 1:2.0 to 2.1:0.43 to 0.48 on a weight basis, respectively.

One or more embodiments include a method of preventing occurrence of inflammation in a subject or improving inflammation in a subject, the method including administrating the composition to a subject.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
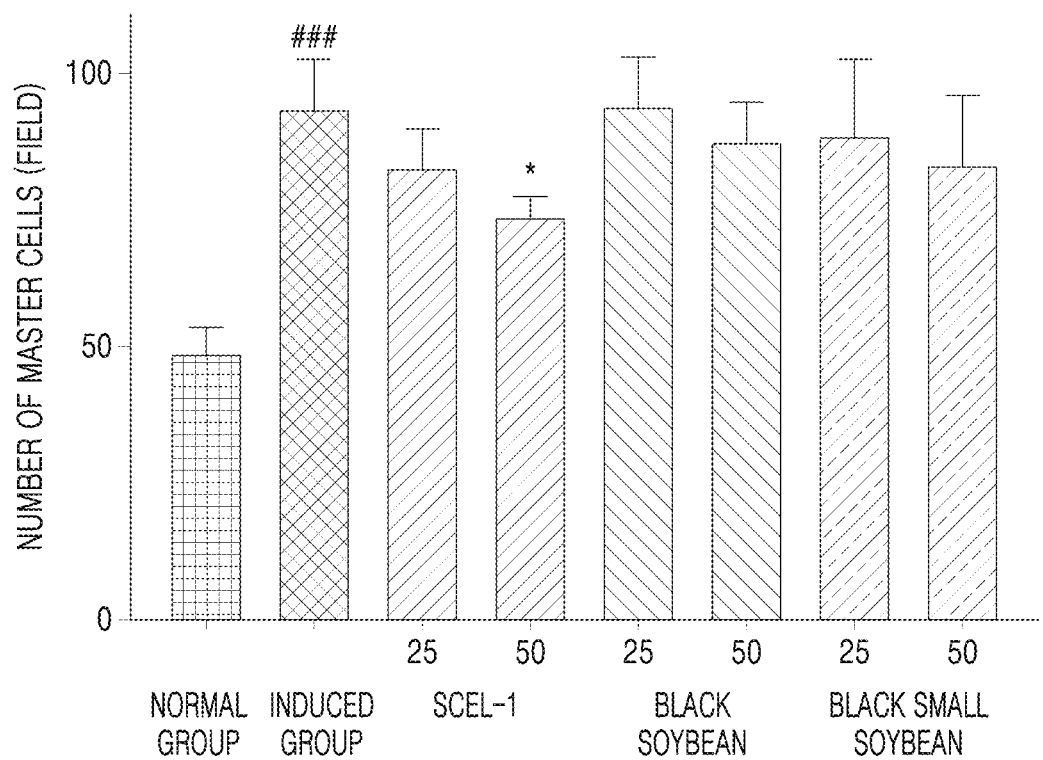
FIG. 1 is a diagram showing effects of improving skin inflammation induced by ultraviolet rays when an extract of a newly selected soybean cultivar is orally administered to a nude mouse.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

A first aspect of the present disclosure provides a composition for preventing or improving inflammation, the composition including, as an active ingredient, an extract obtained by performing an extraction process on a seed of soybean Glycine max (L.) Merrill cultivar SCEL-1 by using water, $C_1$-$C_6$ alcohol, or a mixture thereof, wherein the seed contains cyanidin-3-O-glucoside, procyanidin B2, and epicatechin, wherein an amount of the procyanidin B2 is greater than that of the cyanidin-3-O-glucoside, and a representative sample of the seed is deposited with the Korean Agricultural Culture Collection(KACC), which is an International Depository Authority(IDA) under the Budapest Treaty on the International Recognition of the Deposit of Microorganisms for the Purpose of Patent Procedure under the accession number KACC 88002BP on Nov. 8, 2018. Applicant certifies that that the instant invention will be irrevocably and without restriction released to the public upon the issuance of a patent. The improving inflammation may include treating inflammation in a subject.

In the seed of the present disclosure, cyanidin-3-O-glucoside and procyanidin B2 may be contained at a ratio of 1:2.0 or more, 1:2.0 to 1:5.0, 1:2.0 to 1:3.0, 1:2.0 to 1:2.5, or 1:2.0 to 1:2.1, on a weight basis. The term "amount" as used herein may be calculated based on an extract obtained by pulverizing the seed and incubating the pulverized seed at a temperature in a range of about 25° C. to about 55° C. for 6 hours by using 70 (v/cv) % aqueous ethanol. The term "amount" as used herein is described by way of example, and should be understood as being variable depending on soil, climate conditions, and an individual seed that are considered for production of a plant body of a seed.

In the seed of the present disclosure, a total amount of procyanidin B2 and epicatechin may be, on a weight basis, twice or more or 2.5 times or more, for example, 2.6 times to 5.1 times greater than a weight of a cultivar named Wonheug, which is a standard cultivar.

In the composition of the present disclosure, a total amount of cyanidine-3-O-glucoside, procyanidine B2, and epicatechin in the extract may be in a range of about 2.1% to about 3.4% based on a total weight of the extract, and a total amount of procyanidine B2 and epicatechin in the extract may be in a range of about 1.31% to about 2.4% based on a total weight of the extract.

In the composition of the present disclosure, cyanidin-3-O-glucoside, procyanidin B2, and epicatechin may be contained at a ratio of 1:2.0 to 2.1:0.43 to 0.48 on a weight basis.

In the composition of the present disclosure, an amount of the extract may be in a range of about 0.001% to about 99.9%, about 0.005% to about 99.9%, about 0.01% to about 80.0%, about 0.01% to about 60.0%, about 0.01% to about 50.0%, about 0.01% to about 30.0%, about 0.01% to about 20.0%, about 0.01% to about 15.0%, about 0.01% to about 10.0%, about 0.01% to about 5.0%, about 0.1% to about 99.9%, about 1.0% to about 80.0%, about 5.0% to about 60.0%, about 5.0% to about 50.0%, about 5.0% to about 30.0%, about 30.0% to about 50.0%, about 40.0% to about 80.0%, about 15.0% to about 70.0%, or about 50.0% to about 90.0%, based on a total weight of the composition.

When the seed of the present disclosure germinates and forms a plant body, such a plant body may have characteristics listed in Table 1. Unless otherwise described in the specification, the characteristics of the soybean cultivar may be measured and verified according to "The guidelines for investigation of characteristics of each crop for examination of new varieties: Soybean *Glycine max* (L.) Merrill (Korea Seed Variety Service (KSVS) of the Ministry of Agriculture, Food and Rural Affairs (MAFRA), 2014: http://www.seed.go.kr)", wherein the guidelines determine matters necessary to explain the characteristics of the varieties for each crop in Annex 1 in Article 2 of the Seed Management Guidelines pursuant to Article 30 of the Act of Protection of New Varieties of Plants and Article 33 of the Enforcement Decree of the same Act, and the directions for the qualification tests necessary for cultivation examination according to Article 47 of Enforcement Regulation of the same Act. In addition, unless otherwise described herein, quantitative traits among the characteristics of the soybean cultivar are represented as mean values.

A second aspect of the present disclosure provides a composition for preventing or improving inflammation, the method including, as an active ingredient, cyanidin-3-O-glucoside or a physiologically acceptable salt thereof, procyanidin B2 or a physiologically acceptable salt thereof, and epicatechin or a physiologically acceptable salt thereof at a ratio of 1:2.0 to 2.1:0.43 to 0.48 on a weight basis, respectively. The improving inflammation may include treating inflammation in a subject.

In the composition of the present disclosure, an amount of each of cyanidin-3-O-glucoside or a physiologically acceptable salt thereof, procyanidin B2 or a physiologically acceptable salt thereof, and epicatechin or a physiologically acceptable salt thereof may be in a range of about 0.001% to about 99.9%, about 0.005% to about 99.9%, about 0.01% to about 80.0%, about 0.01% to about 60.0%, about 0.01% to about 50.0%, about 0.01% to about 30.0%, about 0.01% to about 20.0%, about 0.01% to about 15.0%, about 0.01% to about 10.0%, about 0.01% to about 5.0%, about 0.1% to about 99.9%, about 1.0% to about 80.0%, about 5.0% to about 60.0%, about 5.0% to about 50.0%, about 5.0% to about 30.0%, about 30.0% to about 50.0%, about 40.0% to about 80.0%, about 15.0% to about 70.0%, or about 50.0% to about 90.0%.

The composition of each of the first aspect and the second aspect of the present disclosure may be food, a cosmetic composition, or a pharmaceutical composition.

In the second aspect, the expression "physiologically acceptable salt thereof" as used herein includes a meaning of "pharmaceutically acceptable salt thereof". The term expression "pharmaceutically acceptable salt thereof" refers to possible use on animals, more particularly, to humans, without having significant toxic effects when used in a typical medicinal dosage. This expression infers that, for example, one that can be or is approved by a government or regulatory organization equivalent thereto, or one that is listed in the pharmacopoeia or recognized in other general pharmacopoeias.

In the second aspect, the expression "pharmaceutically acceptable salt thereof" refers to a salt according to an embodiment of the present disclosure being pharmaceutically acceptable and having pharmacological activity of a parent compound. Such a salt may include:

(1) an acid addition salt formed of an inorganic acid, such as hydrochloric acid, hydrobromic acid, sulfuric acid, nitric acid, phosphoric acid, or the like; or an organic acid, such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-en-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, muconic acid, or the like; or (2) a salt formed by substitution of an acidic proton in a parent compound.

In the first aspect and the second aspect, the term "active ingredient" refers to an ingredient which exhibits a desired activity alone or an ingredient capable of exhibiting activity with a carrier that is not active by itself.

In the first aspect and the second aspect of the present disclosure, the expression "preventing or improving inflammation" refers to preventing occurrence of inflammation or improving inflammation in tissues including skin in a subject. A cause of the inflammation may include external stress, such as ultraviolet rays or oxidizing agents, in tissues including skin; or internal stress causing occurrence of the inflammation. The tissues may include skin tissues or lung tissues, and the inflammation may include atopic dermatitis or chronic obstructive pulmonary disease (COPD). The improving inflammation may include treating inflammation in a subject.

In the composition for preventing or improving inflammation according to an aspect of the present disclosure, the composition may be also able to prevent or treat skin inflammation or lung inflammation.

In the second aspect of the present disclosure, the composition may include, as an active ingredient, an extract obtained by performing an extraction process on a soybean cultivar seed by using water, $C_1$-$C_6$ alcohol, or a mixture thereof, wherein a representative sample of the soybean cultivar seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

In one embodiment, the composition may be one that is configured to prevent or improve inflammation, and more particularly, may be one that is effective for inflammation caused by external stress, such as ultraviolet rays or oxidative stress, or internal stress.

When the composition of the present disclosure is applied to medicines, the composition may be formulated into an agent in a solid, semi-solid, or liquid form for oral or parenteral administration by adding a commonly used inorganic or organic carrier thereto which includes the composition as an active ingredient.

Examples of the agent for oral administration may include tablets, pills, granules, capsules, powders, infinitesimal grains, emulsions, syrup, pellets, and the like. In addition, examples of the agent for parenteral administration may include injections, instillations, ointments, lotions, sprays, suspensions, emulsions, suppositories, and the like. To formulate the active ingredient of the present disclosure, the active ingredient may be easily formulated according to the conventional method, and a surfactant, an excipient, a coloring agent, a flavoring agent, a preservative, a stabilizer, a buffer, a suspension, and other common adjuvants may be used as appropriate.

The composition according to the present disclosure may be administered orally, parenterally, rectally, topically, transdermally, intravascularly, intramuscularly, intraperitoneally, subcutaneously, and the like.

In addition, a dosage of the active ingredient may vary depending on the age, gender, and weight of a subject to be treated, a particular disease or pathological condition to be treated, the severity of a disease or pathological condition, a route of administration, and a determination made by a prescriber. The determination of the dosage based on these factors may be within a level of one of ordinary skill in the art, and the dosage may be in a range of about 0.001 mg/day to about 2,000 mg/kg/day, more particularly, a range about 0.5 mg/kg/day to about 1,500 mg/kg/day.

Regarding the composition for the prevention or improvement of inflammation according to an aspect of the present disclosure, the composition may include a health food composition.

In one embodiment, the composition may be processed into a drink, fermented milk, a cheese, a yogurt, a juice, a probiotic agent, and a health supplement, each including the composition. In addition, the composition may be used in a variety of other food additives.

In one or more embodiments, the composition may contain other components that exhibit a synergistic effect with main effects within a range that does not damage the intended main effects of the present disclosure. For example, to improve physical properties, the composition may further include an additive, such as a flavoring agent, a dye, a bactericide, an antioxidant, a preservative, a moisturizer, an instillation, an inorganic salt, an emulsifier, or a synthetic polymer. In addition, the composition may further include an adjuvant component, such as a water-soluble vitamin, an oil-soluble vitamin, a polymeric peptide, a polymeric polysaccharide, or a seaweed extract. The components above may be appropriately selected and mixed by one of ordinary skill in the art without difficulty depending on the formulation and purpose of use, and an amount of the components to be added may be selected within a range that does not damage the objects and effects of the present disclosure.

The composition of the present disclosure may be in various forms, such as a solution, an emulsion, a viscous mixture, a tablet, a powder, and the like, and may be administered by various methods using a simple drink, an injection, a spray, or a squeezer.

The composition may include a cosmetic composition, and may be formulated in a parenteral dosage form. An example of the parenteral dosage form may include an injection or an external skin application, and examples of the external skin application may include a cream, gel, ointment, skin emulsifier, skin suspension, transdermal delivery patch, drug-containing bandage, lotion, or any combination thereof.

In the external skin application, components such as typical cosmetics or medicines used for external skin applications, for example, an aqueous component, an oily component, a powder component, an alcohol component, a moisturizer, a thickener, an ultraviolet absorber, a whitening agent, an antiseptic, an antioxidant, a surfactant, a flavoring agent, a dye, various skin nutrients, or any combination thereof, may be appropriately mixed as needed.

In the external skin application, a chelating agent such as disodium edentate, trisodium edentate, sodium citrate, sodium polyphosphate, sodium metaphosphate, gluconic acid, and the like; caffeine, tannin, verapamil, licorice extract, glabridin, hot water extract of calines from fruit, and various herb medicines; medicines such as tocopherol acetate, glycyrrhizic acid, tranexamic acid, or a derivative or salt of any of the foregoing; vitamin C, ascorbic acid magnesium phosphate, ascorbic acid glucoside, arbutin, and kojic acid; and sugars such as glucose, fructose, and trehalose, may be mixed as appropriate.

In the composition for preventing or improving inflammation according to an aspect of the present disclosure, the extract of the soybean cultivar SCEL-1 may be obtained by performing an extraction process on the soybean cultivar SCEL-1 by using water, $C_1$-$C_6$ alcohol, or a mixture thereof. In detail, the extract of the soybean SCEL-1 may be obtained by using methanol, ethanol, propanol, butanol, pentanol, or hexanol.

The extract of the soybean cultivar SCEL-1 of the present disclosure may include a crude extract obtained by performing an extraction process thereon by using a solvent, such as water, $C_1$-$C_6$ alcohol, or a mixture thereof. The $C_1$-$C_6$ alcohol may be, for example, methanol or ethanol. When an extraction process is performed on a soybean by using a solvent, a volume of the solvent may be about 2 times to about 15 times, about 3 times to about 15 times, about 5 times to about 15 times, or about 10 times greater than the soybean. The extraction process may include heat extraction, cold extraction, reflux cooling extraction, or ultrasonic extraction, and there is no limitation as long as the extraction process is obvious to one of ordinary skill in the art. The extraction process may be performed at room temperature, but for better efficient extraction, the extraction process may be performed under warm conditions. For example, the extraction process may be performed at a temperature in a range of about 40° C. to about 100° C., about 40° C. to about 80° C., about 40° C. to about 60° C., or at a temperature of about 50° C. The time for which the extraction process is performed may be in a range of about 2 hours to about 8 hours, about 4 hours to about 8 hours, about 5 hours to about 7 hours, about 5.5 hours to about 6.5 hours, or may be about 6 hours. The temperature may vary depending on conditions including a solvent used for the extraction process. To obtain a greater amount of active ingredients, the extraction process may be performed one or more times. For example, an extract obtained by combining all the extracts from the extraction process performed one to 5 times, one to 4 times, or 3 times consecutively may be used.

The extract of the soybean cultivar SCEL-1 of the present disclosure may include a crude extract of the soybean cultivar SCEL-1, and may be contained as a water-soluble fraction of the organic solvent obtained by further extraction performed on the crude extract.

Examples of the organic solvent may include hexane, methylene chloride, ethyl acetate, n-butanol, and the like. According to the method of the present disclosure, the extract or the water-soluble fraction thereof may be used as it is. In one embodiment, the extract may be used as a concentrate obtained by concentration, and in one or more embodiments, the extract may be used in a lyophilized form obtained by concentration followed by lyophilization.

A third aspect of the present disclosure provides a method of preventing occurrence of inflammation in a subject or improving inflammation in a subject, the method including administrating the composition to a subject.

The administrating may be oral or parenteral administration, and the method according to an aspect of the present disclosure may be able to prevent occurrence of inflammation in a subject or treat inflammation in a subject. The inflammation may include skin inflammation or lung inflammation, and the skin inflammation may include atopic dermatitis.

The method of the present disclosure may include administrating the composition to the skin of a subject. Here, the administrating may include coating or applying the composition to the skin. The method of the present disclosure may be considered as a make-up method, and may prevent or reduce the occurrence of reactive oxygen species (ROS) in the skin. The ROS may be produced when ultraviolet rays are irradiated to the skin.

The subject may include a mammal including a vertebrate, or fish. The vertebrate may include a cow, a pig, a cat, a dog, or a sheep. That is, the subject may be a mammal other than a human.

Hereinafter, the present disclosure will be described in detail with reference to the following Examples. However, these Examples are for illustrative purposes only, and the scope of the present disclosure is not intended to be limited thereby.

Examples 1: Breeding and Characteristics of New Cultivar

1. Breeding of Cultivar 20 soybean seed grains, which are black flat-shaped granules collected as genetic resources from Idong-eup, Yongin-si, Gyeonggi-do, Korea, were prepared. As a result of cultivating the soybean seeds, separation occurred in terms of shape and color of the flowers, and in this regard, it was confirmed that the traits of the soybean seeds were not fixed. For example, the flower color appeared separately as white or pink. In this regard, the traits of the soybean seeds did not seem to be fixed, and thus, the soybean seeds were not recognized as species due to lack of stability and uniformity.

Therefore, the inventors of the present disclosure bred a cultivar by using the soybean seeds according to a pure line selection breeding method. The pure line selection was carried out from 2013 to 2017, and more particularly, it was carried out by the whole crop experimental field in the Rural Development Administration (RDA): National Institute of Crop Science (NICS) located in Suwon, Republic of Korea from 2013 to 2014, and then, in the field located in Iseo-myeon, Wanju-gun, Republic of Korea from 2015 to 2017.

A specific process of the pure line selection from the collected genetic resources of the soybean is as follows: as genetic resources, 20 soybean seeds were sown at the beginning of June every year from 2013 to 2016 in the experimental field affiliated with the RDA; then, 1 seed was selected for the purity improvement at the end of November and then harvested as a sowing seed for the following year. After four years of the pure line selection process, one finally fixed pure line seed was selected.

To confirm uniformity, traits, such as hypocotyl color, flower color, trichome color, legume color, leaf shape, growth type, flowering periods, and maturity, were examined every year. In the pure line separation process performed on the collected genetic resources, separation was observed in the hypocotyls color and the flower color in 2013, whereas no separation was observed with respect to the other traits. In addition, the progeny selected in 2013 was found to maintain uniformity in target traits among traits examined from 2014 to 2017. The distinguishable features between a standard cultivar (named Wonheug) and a control cultivar (named Cheongja-3) are clearly shown in Table 1 in terms of growth type, days to flowering, hypocotyl color, weight of 100 beans, and leaf shape. Table 1 shows the characteristics of the finally selected pure line. In Table 1, the finally selected line (cultivar) was named SCEL-1. FIG. 4 is a photograph of seeds of the finally selected cultivar SCEL-1.

TABLE 1

| Source | Growth type (determinate, indeterminate) | Number of days to flowering | Flower color (violet or white) | Hypocotyl color (violet or green) | Trichome color (brown, light gray) | Testa | Hilum color | 100-seed weight (g) | Leaf shape |
|---|---|---|---|---|---|---|---|---|---|
| Wonheug (standard) | Determinate | 66 | Violet | Violet | Brown | Black | Black | 11.6 | Globular |
| Cheongja-3 (control) | Determinate | 70 | Violet | Violet | Brown | Black | Black | 40.7 | Globular |
| Selected cultivar (SCEL-1) | Indeterminate | 58 | White | Green | Brown | Black | Black | 8.8 | Oblique ellipse |

2. Identification of Cultivar Characteristics Relative to Control Cultivar

To compare the agricultural performance of the finally selected pure line cultivar SCEL-1 relative to the existing cultivars, the performance of each cultivar was identified by repeating the randomized block design three times by using the Wonheug bean as a standard cultivar and Cheongja-3 as a control cultivar in the field affiliated with the NISC in summer of 2017. Here, the agronomic traits of each cultivar were examined by cultivating plants after sowing two seeds per hole (60 cm×15 cm) containing four rows (4 meters long) in an experimental plot on Jun. 8, 2017, and then cultivating the seeds. The Wonheug bean (Cultivar Application Publication Number: 2010-341) is a *microcarpa* bean cultivar with a black seed coat developed by the NICS in 2009, and is currently the most cultivated cultivar in farming. The Wonheug bean is similar to the selected cultivar SCEL-1, and thus, may be used as a standard cultivar for the comparison. The control cultivar, Cheongja-3 (Cultivar Application Publication Number: 2005-176), was developed by the NICS in 2004 and is a soybean cultivar that has a black seed coat, is large-sized, and is used for cooking with rice. The Wonheug bean and Cheongja-3 are commercially available from the Korean Seed and Variety Service (KSVS) or the like.

The agronomic traits and traits examined for the performance testing were examined mainly in terms of yield component traits, such as stem length, number of nodes, number of branches, and the like. To examine such yield component traits, 10 plants within each experimental plot were examined during a maturation period in terms of stem length, number of nodes, number of branches, number of pods, 100-seed weight, yield per plant, yield per area, and yield per 10 acres (a).

Tables 2 and 3 show the characteristics of the selected soybean cultivar, the standard cultivar, and the control cultivar.

number of pods, the constitution ratio of the 1-pod, 2-pods, and 3-pods was similar to the standard cultivar. Regarding the total number of pods, the number of grains, the yield per plant, and the yield per area, which indicate the yield component traits, the selected cultivar had 184 pods, 397 grains, 23.1 g of the yield per plant, and 4.6 g of the yield per are, wherein the resulting numbers and yields were lower than those of the standard cultivar. Here, 100 grains were weighed at 9.4 g, and in this regard, the selected cultivar had small grains as compared with the standard cultivar. When the yield per 10a was calculated based on the results above, the selected cultivar showed 413 kg/10 a, which was only about 70% of the yield per 10a of the standard cultivar, Wonheug. However, the amounts of procyanidin B2 and epicatechin, which are functional substances, were about 301% and 217%, respectively. In detail, the amount of procyanidin B2 was 149.4 ug/100 mg, 49.5 ug/100 mg, and 34.3 ug/100 mg in the selected cultivar SCEL-1, Wonheug, and Cheongja-3, respectively. The amount of epicatechin was 46.9 ug/100 mg, 21.6 ug/100 mg, and 20.1 ug/100 mg in the selected cultivar SCEL-1, Wonheug, and Cheongja-3, respectively. Here, the amounts of procyanidin B2 and epicatechin were confirmed by an extraction process performed according to the method of Section 1 in Example 2.

According to the experiments, the cultivar SCEL-1 was found to have high uniformity and was distinguished from the standard cultivar and the existing cultivars by the comparison, and was also able to be recognized as an independent cultivar with distinct characteristics in terms of the agronomic traits, the yield ability, and the functional material contents.

TABLE 2

| Source | Stem length (cm) | Number of nodes | Number of branches | Seed number per pod | | |
|---|---|---|---|---|---|---|
| | | | | 1 pod | 2 pods | 3 pods |
| Wonheug (standard) | 56.6 ± 4.3 | 14.7 ± 1.7 | 6.7 ± 2.1 | 18.8 ± 2.3 | 201 ± 21 | 32 ± 15.2 |
| Cheongja-3 (control) | 71.9 ± 2.7 | 14.1 ± 0.3 | 7.3 ± 0.6 | 13.8 ± 4.9 | 81 ± 12 | 4.7 ± 0.8 |
| Selected cultivar (SCEL-1) | 82.9 ± 1.4 | 15.8 ± 0.5 | 6.4 ± 0.3 | 12.9 ± 2.3 | 133 ± 44 | 38.3 ± 8.6 |

TABLE 3

| Source | Total number of pods | Number of grains | 100-seed weight (g) | Yield per plant (g) | Yield per area (kg) | Yield per 10 acre (a) (kg) |
|---|---|---|---|---|---|---|
| Wonheug (standard) | 252 ± 31 | 512 ± 70 | 11.6 ± 0.2 | 32.9 ± 3.3 | 6.6 ± 0.7 | 587 ± 60 |
| Cheongja-3 (control) | 100 ± 12 | 191 ± 25 | 40.7 ± 3.1 | 26.7 ± 3.2 | 5.3 ± 0.6 | 477 ± 57 |
| Selected cultivar (SCEL-1) | 184 ± 54 | 397 ± 113 | 9.4 ± 0.4 | 23.1 ± 2.0 | 4.6 ± 0.4 | 413 ± 36 |

Referring to Tables 2 and 3, it was found from the examination that the selected cultivar was longer than the standard cultivar, Wonheug, by 26 cm, and had one more node than the standard cultivar, Wonheug. In addition, regarding the number of branches, it was found from the examination that the selected cultivar was had about 6.4 branches similar to the standard cultivar, and regarding the This newly selected cultivar of a black small-sized bean having an oblique ellipse shape was named SCEL-1, and was deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018. FIG. 1 shows a schematic breeding diagram of a soybean cultivar according to the present disclosure.

Example 2: Extract Obtained by Performing an Extraction Process on a Newly Selected Soybean Seed by Using Water, Alcohol, or a Mixture, and Use of the Extract In this Example, an extract was prepared from a seed of the newly selected soybean cultivar SCEL-1 of Example 1, and an effect of the extract was identified.

1. Preparation of an Extract

Immediately before analyzing a seed of the selected cultivar, the seed was pulverized by using a high-speed pulverizer (Wonder Blender, 820W, 30000 RPM, Sanplatec Corp) to prepare powdered seed. 1 g of the powdered seed thus obtained was mixed with 100 ml of 70 (v/v) % aqueous ethanol in a glass tube, and the mixed solution was stirred at a temperature of 55° C. for 6 hours by using a magnetic bar. Then, the resulting extract was filtered through filter paper (Garde No. 131 Qualitative filter paper, Advantec).

Afterwards, the ethanol layer was dried in a nitrogen gas drier (hurricane-Eagle, Chongmin Technology) for 1 hour, and then, was lyophilized for one day to completely remove moisture, thereby obtaining 0.19 g (standard deviation SD: ±0.015) of a soybean extract. In the experiments, for use of the soybean extract, it was dissolved at a concentration of 30 mg/ml in 50% v/v ethanol, and was subjected to the HPLC analysis.

2. Confirmation of Inflammation Improving Effect (1) Improvement of Skin Inflammation by Oral Administration When orally administering the extract obtained in Section 1, the efficacy of the extract of improving skin inflammation induced by ultraviolet rays was confirmed through an experiment using a nude mouse model.

8-week-old nude mice (OrientBio, SKH-1 species, and average weight of 26.2 g) were divided into two groups, each having seven mice. Here, one group is a control group, and the other group is a test group. In the test group, based on a weight, 2.5 mg/10 ml and 5.0 mg/10 ml of an extracted solution were each administered to a mouse to be 25 mg/kg/day and 50 mg/kg/day, respectively, wherein the extracted solution was obtained by dissolving the lyophilized extract of Section 1 in an aqueous solution containing 2% ethanol, 1% Tween 80, and 0.8% carboxymethyl cellulose (CMC). In the control group, based on a volume, an aqueous solution containing 2% ethanol, 1% Tween 80, and 0.8% CMC was administered to a mouse. Here, the administration was performed by direct administration to the stomach of the mouse using an oral zoned. In this regard, the soybean extract was able to be administered to the mouse at doses of 25 mg/kg/day and 50 mg/kg/day.

After the administration of the extract, ultraviolet ray was irradiated to the mouse. In detail, to individual mice in each of the control group and the test group, 1 minimal erythema dose (MED) of ultraviolet ray was irradiated three times a week for two weeks, 2 MEDs of ultraviolet ray was irradiated three times a week for two weeks, 3 MEDs of ultraviolet ray was irradiated twice a week for two weeks, and 4 MEDs of ultraviolet ray was irradiated twice a week for two weeks. That is, the irradiation was performed for a total of eight weeks. Afterwards, the skin tissue of the nude mouse out of the experiment was treated with formalin. Then, to measure infiltration of inflammatory cells, the treated skin tissue was stained with toluidine blue, and the results are shown in FIG. 1 and Table 4. In Table 4 and FIG. 1, the number of master cells that are inflammatory cells existing after the extract of soybean SCEL-1 was administered to the mouse are shown.

TABLE 4

| Sample | Oral dose (mg/kg/day) | Number of master cells/dermis (%) |
| --- | --- | --- |
| Untreated group | 0 | 49.1 ± 4.7 |
| UVB (40 mJ/cm$^2$)-induced group | 0 | 93.2 ± 9.3 |
| Soybean SCEL-1 | 25 | 82.5 ± 7.1 |
|  | 50 | 73.5 ± 4.2 |
| Black soybean | 25 | 93.8 ± 8.9 |
|  | 50 | 87.5 ± 7.1 |
| Small black soybean | 25 | 88.5 ± 12.8 |
|  | 50 | 82.9 ± 13.9 |

Referring to Table 4 and FIG. 1, a test group treated with the soybean SCEL-1 showed that the activity of reducing and restoring the skin inflammation induced by ultraviolet irradiation was significantly better than that of general black soybeans.

Referring Table 4, the general black soybean which is similar to Cheongja-3 was purchased at Nonghyup of Gyeongpo branch in Gangneung, Republic of Korea. The Rhynchosia nulubilis which was similar to Wonheug was purchased at Nonghyup of Chiak Mountain branch in Wonju, Republic of Korea. The extract of each sample was obtained by the same extraction process performed on the soybean SCEL-1.

From the results above, it was confirmed that the oral administration of the extract of soybean SCEL-1 showed excellent effects in preventing the destruction of the skin tissue or anti-skin inflammation, each induced by ultraviolet ray.

(2) Treatment of Atopic Dermatitis

In a mouse, oxazolone was administered thereto to induce an oxazolone-induced atopic dermatitis. Then, the effect of the extract of the selected cultivar on atopic dermatitis was examined.

In detail, mice (male, 20 g, 8-week-old, Central Lab. Animal Inc.) was divided into a group of 6, and each group was named as a control group, a induction group (Vehicle), a positive control group (Dexa), a soybean SCEL-1 0.1% (w/v)-treated group, a soybean SCEL-1 0.3% (w/v)-treated group, a SCEL-1 1.0% (w/v)-treated group, and a general black soybean (available from Nonghyup of Gangneung-kyo-1-dong) 1.0% (w/v)-treated group. Each sample was prepared in the same manner as in Section (1).

To induce atopic dermatitis in mice, 40 μl of 1% oxazolone per ear was applied once a day. After one week and starting from the eighth day, 40 μl of 1% oxazolone per ear was applied on alternate days for three weeks. In addition, starting from the eighth day, in addition to the oxazolone application, samples were also applied twice a day. Immediately after the experiment, a tissue of the ear was immobilized in 10% paraformaldehyde for 24 hours or more, and then, immersed in paraffin to form a block. The block was then fixed, and cut to a thickness of 10 μm by using a microtome that enables cutting to a constant thickness. A section of the obtained tissue was adhered to a glass slide, deparaffinized, and then, stained with haematoxylin and eosin (H&E) for the observation with an optimal microscope. Accordingly, the induction and mitigation efficacy on atopic dermatitis was histologically confirmed.

Figure 2:
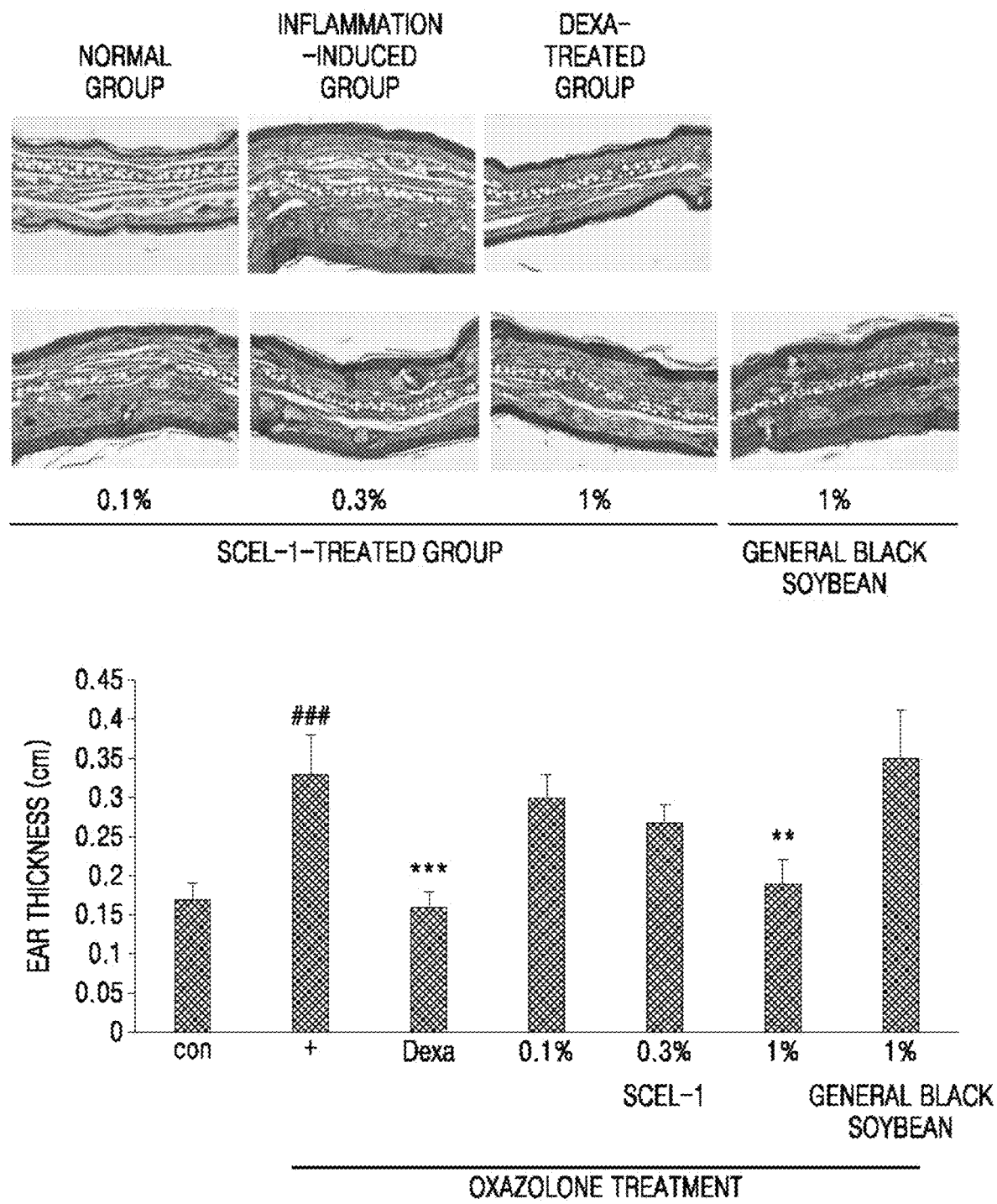
FIG. 2 is a diagram showing improvement effects of treating atopic dermatitis when an extract of a newly selected soybean cultivar is applied to the skin after oxazolone-induced atopic dermatitis is caused on the skin.

FIG. 2 is a diagram showing the effect of the extract of the selected soybean cultivar on the ear thickness of the mouse having oxazolone-induced atopic dermatitis, when the extract was administered to the mouse. As shown in FIG. 2, a thickness of the ear skin was significantly increased due to inflammation when animal inflammation was induced. When treated with dexamethanosone (Dex) which is an anti-inflammatory drug used for skin inflammation, it was confirmed that a thickness of the ear skin was reduced to a thickness near the normal level. Furthermore, it was confirmed that, when treated with the extract of the selected soybean cultivar at 1% which is low as compared to the inflammation-induced group, the ear thickness was significantly reduced by the inflammation. Meanwhile, it was also observed that, when treated with the extract of the general black soybean at 1% which is the same level as the extract of the selected soybean cultivar, the extract of the general black soybean at was not able to reduce the ear thickness that was increased by the inflammation.

According to the results above, it was confirmed that the extract of the selected soybean cultivar exhibits effects of treating inflammation.

3. Analysis of Components of Soybean Extract

The soybean extract was subjected to mass spectrometry, so as to analyze active ingredients in the soybean extract.

In detail, the analysis of components in the soybean extract was carried out by using an Agilent 1260 HPLC system and a Bruker MicrOTOF-Q II mass spectrometer. Here, for the column analysis, a Prevail $C_{18}$ column (250 mm×4.6 mm, 5 um), Solvent A of a mobile phase consisting of 95% water/5% acetonitrile (0.1% formic acid), and Solvent B of a mobile phase consisting of 95% acetonitrile/5% water (0.1% formic acid) were used. Here, the flow rate of the solvent was set at 0.7 ml/min, and the concentration gradient conditions of the solvent used for the separation of components are shown in Table 5.

TABLE 5

| Time (min) | A (%) | B (%) | Flow rate (ml/min) | Maximum pressure (bar) |
| --- | --- | --- | --- | --- |
| 0.00 | 95.00 | 5.00 | 0.700 | 1000.00 |
| 3.00 | 95.00 | 5.00 | 0.700 | 1000.00 |
| 23.00 | 50.00 | 50.00 | 0.700 | 1000.00 |
| 28.00 | 0.00 | 100.00 | 0.700 | 1000.00 |
| 33.00 | 0.00 | 100.00 | 0.700 | 1000.00 |
| 33.10 | 95.00 | 5.00 | 0.700 | 1000.00 |
| 40.00 | 95.00 | 5.00 | 0.700 | 1000.00 |

Here, the temperature of the column was maintained at 35° C., and 10 μL of the sample was injected into the column. A mass spectrometer was used to analyze ingredients contained in the soybean extract under conditions of mode: ESI(+); mass range: 50 m/z to 800 m/z; nebulizing gas: 8 L/min; source gas temperature: 180° C.; capillary voltage: +4,500 V; and cone voltage: 35 V.

As a result, the amount of each of epicatechin and procyanidin B2 contained in the selected cultivar named SCEL-1 was in a range of about 0.32% to about 0.46% and in a range of about 1.0% to about 2.0%, respectively, which was significantly higher than the amounts thereof in Wonheug, which were respectively in a range of about 0.14% to about 0.15% and in a range of about 0.33% to about 0.35%.

In cultivar named SCEL-1 selected on the basis of cyanidin-3-O-glucoside which is a representative substance of anthocyanin antioxidants, cyanidin-3-O-glucoside, procyanidin B2, and epicatechin were contained at a ratio of 1:2.0 to 2.1:0.43 to 0.48. Meanwhile, in Wonheug, cyanidin-3-O-glucoside, procyanidin B2, and epicatechin were contained at a ratio of 1:0.43 to 0.70:0.19 to 0.25.

According to the one or more embodiments, a composition for preventing or improving inflammation, the composition including an extract of soybean cultivar SCEL-1, may be used to prevent or improve inflammation.

According to the one or more embodiments, a method of preventing occurrence of inflammation in a subject or improving inflammation in a subject may be used to prevent occurrence of inflammation in a subject or improve inflammation in a subject.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of treating a human suffering from atopic dermatitis or chronic obstructive pulmonary disease, the method comprising administering a composition to the human in need thereof,
   wherein the composition comprises, as an active ingredient, an extract obtained by performing an extraction process on a seed of soybean Glycine max (L.) Merrill cultivar SCEL-1 by using water, $C_1$-$C_6$ alcohol, or a mixture thereof,
   wherein the extract contains cyanidin-3-O-glucoside, procyanidin B2, and epicatechin,
   wherein an amount of procyanidin B2 contained in the extract by weight is two times or more than an amount of cyanidin-3-O-glucoside contained in the extract by weight, and
   wherein a representative sample of the seed is deposited with the Korean Agricultural Culture Collection (KACC), which is an International Depository Authority (IDA) under the Budapest Treaty on the International Recognition of the Deposit of Microorganisms for the Purpose of Patent Procedure under the accession number KACC 88002BP on Nov. 8, 2018.

2. The method of claim 1, wherein a total amount of the cyanidin-3-O-glucoside, procyanidin B2, and epicatechin in the extract is in a range of 2.1% to 3.4% based on a total weight of the extract.

3. The method of claim 1, wherein the extract comprises a mass ratio of cyanidin-3-O-glucoside:procyanidin B2 to be between 1:2.0 and 1:2.1.

4. The method of claim 1, wherein an amount of the extract is in a range of 0.005% to 99.9% based on a total weight of the composition.

5. The method of claim 1, wherein the human is also suffering from skin inflammation.

6. The method of claim 1, wherein the composition is a food, a cosmetic composition, or a pharmaceutical composition.

* * * * *